Figure 9:
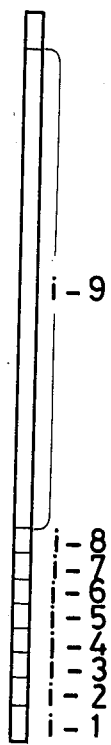

United States Patent [19]

Hibino et al.

[11] Patent Number: 4,690,907

[45] Date of Patent: Sep. 1, 1987

[54] CAPILLARY TUBE IMMUNOASSAY

[75] Inventors: Mitsugu Hibino; Taira Kanada; Miyoshi Hirata, all of Tokyo, Japan

[73] Assignee: Daiichi Pure Chemicals Co., Ltd., Tokyo, Japan

[21] Appl. No.: 683,628

[22] Filed: Dec. 19, 1984

[30] Foreign Application Priority Data

Dec. 19, 1983 [JP] Japan ................................ 58-239549
May 8, 1984 [JP] Japan ................................ 59-91379

[51] Int. Cl.$^4$ ................. G01N 33/558; G01N 33/557; G01N 33/543; G01N 33/551
[52] U.S. Cl. ........................... 436/514; 436/515; 436/518; 436/524; 436/527; 422/56
[58] Field of Search .............. 436/514, 515, 527, 524, 436/532, 518, 535; 422/56

[56] References Cited

U.S. PATENT DOCUMENTS

| | | | |
|---|---|---|---|
| 4,116,638 | 9/1978 | Kenoff ................................ | 436/527 |
| 4,235,601 | 11/1980 | Deutsch et al. .................... | 436/514 |
| 4,305,924 | 12/1981 | Piasio et al. ....................... | 424/1 |
| 4,447,546 | 5/1984 | Hirschfeld ......................... | 436/527 |

Primary Examiner—Robert J. Warden
Assistant Examiner—Patricia L. DeSantis
Attorney, Agent, or Firm—Oblon, Fisher, Spivak, McClelland, & Maier

[57] ABSTRACT

A component of a sample may be detected or quantitatively measured by an immunoreaction, namely causing a target substance-immunoreactive reagent labelled with a marker-reaction product and/or any remaining, unreacted, immunoreactive reagent to move while making use of capillarity, causing the reaction product or any remaining, unreacted, immunoreactive reagent to combine with a substance packed in a capillary tube, and is immobilized on a carrier and adapted to uptake labelled substance so as to immobilize the reaction product or any remaining, unreacted, immunoreactive reagent, and measuring the amount of the thus-immobilized labelled substance. Since reagents are all filled in the capillary tube, there is no such troublesome that the reagents have to be prepared and/or any extra reagents have to be discarded upon conducting the measurement. The immunoassay may be carried out at bed side in hospitals. An extremely small amount of the sample may be sufficient for its measurement. After the measurement, the capillary tube may be stored as is or may be thrown away with ease.

5 Claims, 16 Drawing Figures

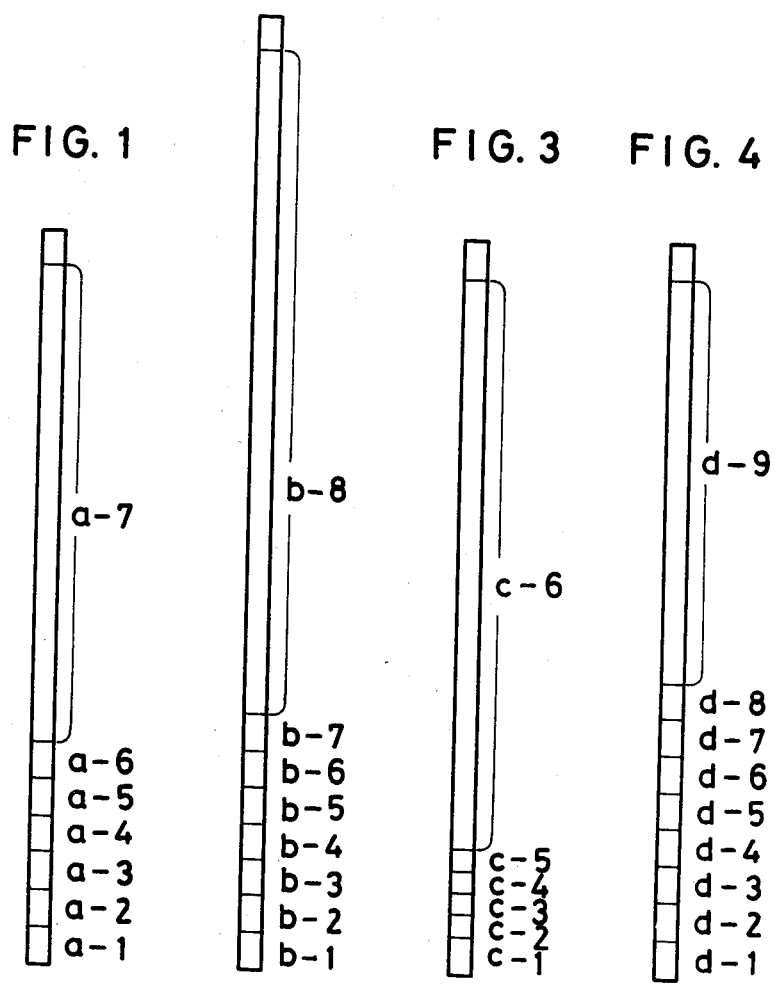

FIG. 5   FIG. 6   FIG. 7   FIG. 8
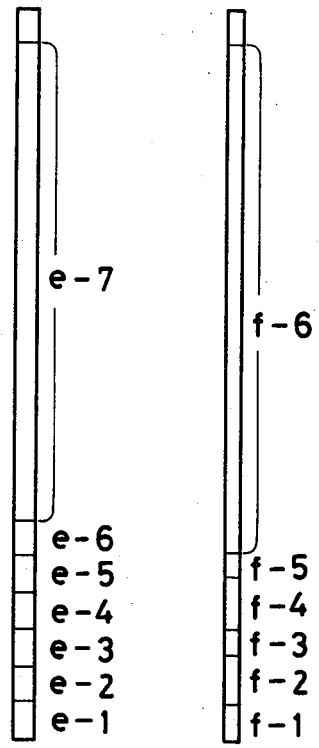
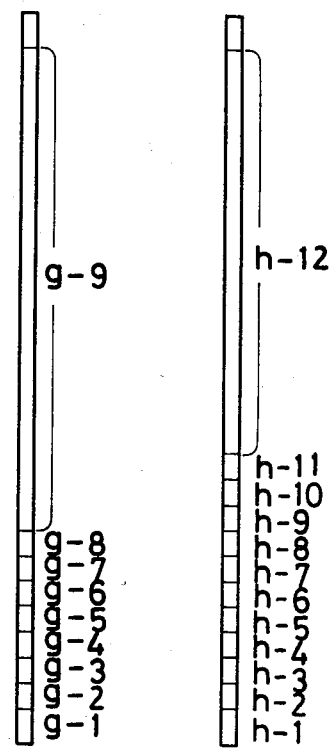

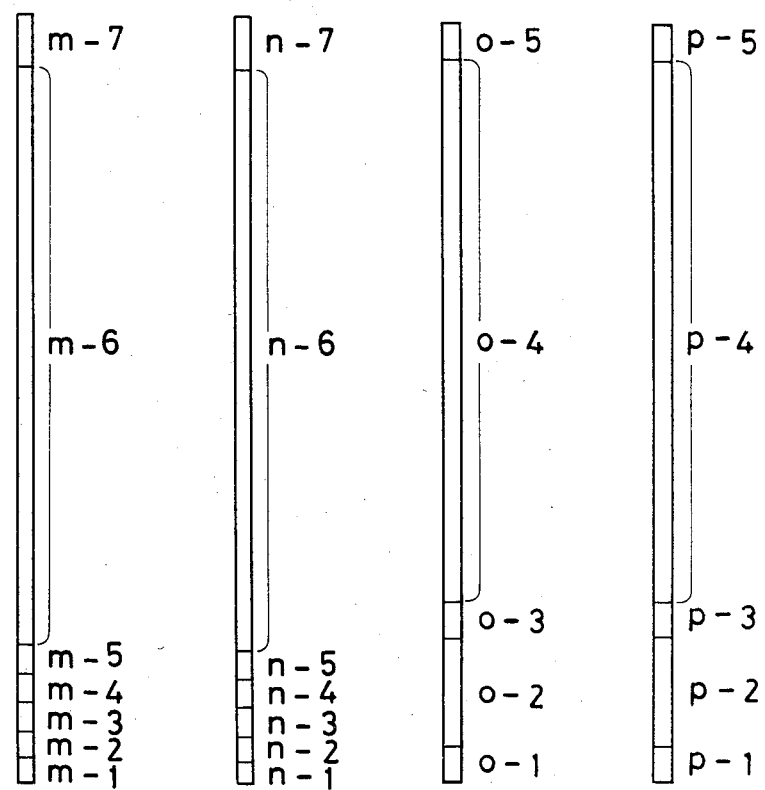

CAPILLARY TUBE IMMUNOASSAY

This invention relates to a method for detecting or quantitatively analyzing a component in a sample in accordance with an immunoreaction, particularly the antigen-antibody reaction as well as the reaction with marker labelled substance are carried out in a capillary tube.

Conventional immunoassay techniques employ antigens labelled with radioactive substance, enzyme, fluorogenic substances or the like, or antibodies labelled with radioactive substances, enzyme, fluorogenic substances or the like. The labelled substances were then subjected to immuno-reactions with antibodies or antigens in a sample respectively. The immuno-reacted labelled substances were then detected or quantitated by detecting or quantitating their labels, i.e. radioisotopes, enzymes, fluorescent substances or the like.

It is necessary for these conventional immunoassay techniques to separate the reacted labelled or unlabelled substances and their corresponding unreacted labelled or unlabelled substances from each other, in order to define quality or quantity of the sought antigen or antibody. Thus, these conventional techniques were accompanied by such drawbacks that they require cumbersome operations, professional skill and time-consuming steps for the above-mentioned separation.

The present inventors have hence carried out an extensive research with a view toward solving such drawbacks of the conventional techniques. As a result, it has been found that a component present in a sample may readily be detected or even quantitatively analyzed in a short period time by causing the marker-labelled substance with or without immunoreaction with the component in a sample to move from one zone and then uptaking and immobilizing them selectively at different zones in the capillary tube while making use of capillarity or the like as well as using an immobilizing and uptaking substance for the labelled substance. Based on the above finding, the present invention has been brought to completion.

Accordingly, this invention provides an immunoassay adapted to detect or quantitatively analyze a component in a sample in accordance with an immunoreaction, characterized in that a target substance, labelled immunoreactive reagent, and/or other immunoreactive reagent are caused to move through a capillary tube either as unreacted form or as immunocomplexes while making use of capillarity; the reaction product or the unreacted immunoreactive reagent is combined with a substance which has been packed in the capillary tube and immobilized on a carrier and is adapted to take up the labelled substance; and the amount of the thus-immobilized labelled substance is then measured.

In the immunoassay of this invention, the uptaking of each labelled substance can be carried out in a capillary tube, thereby bringing about the following various advantages:

(1) Since reagents are all filled in a capillary tube, there is no such troublesome that the reagents have to be prepared and/or any extra reagents have to be discarded upon conducting the measurement as encountered with the conventional techniques.

(2) It is possible to detect or quantitatively analyze the target component in the sample merely by dipping the lower end of the capillary tube in a solution of the sample. This procedure is extremely simple and anyone can thus conduct the measurement of the target component without need for professional skill. Moreover, this measurement does not require any additional devices or facilities and can be performed in an extremely short period of time.

(3) Therefore, the measurement may be carried out at bed sides in hospitals.

(4) An extremely small amount of each sample may be sufficient for its measurement. For the measurement of blood components for example, it is only necessary to prick an ear lobe, bringing the lower end of a capillary tube into contact with the cut portion and then soaking the blood into the capillary tube.

(5) After the measurement, the capillary tube may be stored as is or may be discarded with ease.

The above and other objects, features and advantages of this invention will become apparent from the following description and appended claims, taken in conjunction with the accompanying drawings, in which:

FIG. 1 through FIG. 16 illustrate capillary tubes useful for measurement in the present invention.

Exemplary, antigenic components present in samples which components are to be measured in accordance with this invention are those contained in organism constituents, such as immunoglobulin, Bence-Jones protein, $\alpha_1$-antichymo-trypsin, $\alpha_1$-antitrypsin, $\alpha_1$-microglobulin, $\alpha_2$-microglobulin, $\beta_2$-microglobulin, haptoglobin, ferritin, transferrin, ceruloplasmin, antithrombin III, myoglobin, myosin light chain, cryoglobulin, calmodulin, prealbumin, albumin, transcortin, tyroxine-binding proteins, retinol-binding proteins, hemopexin, fibronectin, specific pregnant glycoprotein (SPI), and so on; enzymens including GOT, GPT, ALP, ACP, LDH, $\gamma$-GTP, creatine kinase, LAP, amylase, macroamylase, cholineesterase, aldolase, MAO, 5'-nucleotidase, acid phosphatase, OCT, pancreatic lipase, plasminogen activator, catalase, L-CAT, lipoprotein lipase, phospholipase A, DNase, RNase, terminal transferase, pepsin, trypsinogen, chymotrypsin, enterokinase, aminopeptidase, peroxidase, enolase, tyrosine hydroxylase, dopa decarboxylase, dopamine $\beta$-hydroxylase, etc.; carbohydrates including acidic mucopolysaccharides, inulin, ganglioside, mucopolysaccharides and so on; lipids, for example, cholesterol, lipoproteins, apolipoproteins, triglyceride, free fatty acids, phospholipids, bile acid, peroxidelipids, etc.; vitamins inclusive of vitamin A, D, E and K, ubiquinone, thiamine, riboflavin, vitamin $B_6$, nicotinic acid, folic acid, vitamin $B_{12}$, ascorbic acid, inositol, and so on; coagulation factors including fibrinogen, FDP, plasminogen, Factor VIII, Factor IX, Factor XI, Factor XII, prothromboplastin factor, Factor III, Factor V, Facrtor VII, Factor X, prothrombin, $\beta$-tromboglobulin, $C_1$ inhibitor, $\beta_2$ macroglobulin, $\alpha_2$ plasmin inhibitor, platelet factor 4, platelet membrane protein, protein C, etc.; pituitary secretion substances, e.g., growth hormone (somatotropin), somatomedin, luteinizing hormone, follicle-stimulating hormone, adrenocorticotropic hormone (ACTH), LPH, MSH, $\beta$-endorphin, enkephalin, thyrotropic hormone, prolactin, vasopressin, neurophysin, oxytocin and the like; thyroid gland secretion substances, for example, $T_4$, total thyroxine, free thyroxine index, free thyroxine, triiodothyronine, reverse $T_3$, long-lasting thyroid stimulating hormone, calcitonin, thyroglobulin, and the like; adrenal medulla and sympathetic seretion substances including cathecol amine, metanephrin, normetanephrin, vanillylmandelic acid, homovanillic acid, 3,4-dihydroxyphenylalanine, 3,4-dihydroxyphenylacetic acid, 3-methoxy-4-hydroxyphenylethylene glycol, dopamine-$\beta$-hydroxylase, etc.; adrenal cortex secretion substances, e.g., aldosterone, 11-deoxycorticosterone, corticosterone, 18-hydroxycorticosterone, cortisol, 11-deoxycortisol, 11-hydroxycorticosteroid, 17-hydroxy $C_{21}$-steroid, dehydroepiandrosterone, dehydroepiandrosterone sulfate, androstenedione, 17-ketosteroid, and so on; germinal gland and placenta excretion substances, for example, testosterone, 5$\alpha$-dihydrotestosterone, androstenedione, estrone, estradiol, estriol, estetrol, cathecol estrodiene, progesterone, pregnanediol, 17-a-hydroxyprogesterone, pregnanetriol, chorionic gonadotropin, placental lactogen, and the like; pancreas and digestive secretion substances, including insulin, proinsulin, C-peptide, pancreatic glucagon, gastrin, secretin, CCK-PZ, Motilyn, enteroglycagon, pancreatic polypeptides, somatostatin, substance P, neurotensin, etc.; antigens used in syphitis tests and immunoserologic tests of pathogenic microorganisms; virus, e.g., antimycoplasma antibody, rickettsia, anti-streptlysin 0, anti-streptokinase, anti-deoxyribonucleokinase B, hypes simplex virus, varicella and herpes zoster virus, cytomegalovirus, EB virus antibody, adenovirus, influenza virus A and B, influenza virus C, parainfluenza virus, RS virus, mumpsvirus, measles virus, rubella virus, Japanese encephalitis virus, polio virus, hepatitis virus A, hepatitis virus B, hepatitis virus S, E, C, non-A and non-B, rhinovirus, coronavirus, extrinsic infectious diseases, rebies, mumps, coxsackie virus, chlamydia, Rota virus, etc.; autoantibodies, for example, antinuclear antibody, anti-DNA antibody, anti-ENA antibody, rheumatoid factor, antiglobulin, LE cells, anti-mitochondria, anti-smooth muscle antibody, antistomach wall antibody, anti-intrinsic factor antibody, anti-cross-striated muscles antibody, anti-heart muscle antibody, antiadrenal cortex antibody, antithyroglobulin antibody, antithyroid microsome antibody, antiinsulin antibody, antiinsulin receptor antibody, antiacetylcholine receptor antibody, etc.; cell substances including $\beta$1E globulin, complements such as $C_{1q}$, $C_{1r}$, $C_{1s}$, $C_2$, $C_3$, $C_4$, $C_5$, $C_6$, $C_7$, $C_8$, $C_9$ and the like, T cells, B cells, macrophage and so on; tumor markers, e.g., carcinoembryonic antigens, $\alpha$-fetoprotein, basic fetoprotein, ferritin, isoferritin, polyamines, CRP, immunoacetic protein (IAP), pancreoembryonic antigens (POA), death factor, etc.; drugs including phenobarbital, primidone, phenytoin, carbamazepine, valproic acid, lidocaine hydrochloride, digoxin, digitoxin, theophilline, deisopyramide, mexiretine, propranolol hydrochloride, diuretics, synthetic steroid agents, chloramphenicol drugs, aminoglycoside drugs, antituberculosis drugs, methotrexate, opiate, methadone, barbital, amphetamine, cocaine metabolites, benzodiazopine metabolites, protoxyphene, phencyclidine, cannabinoid, etc.; renin/angiotenin HCAs including renin, angiotensinogen, angiotensin I, II and III, angiotensin-converting enzymes, kinin, kininogen, plasma kallikrein, glandular kallikrein and the like; antigens for blood group tests and blood matching tests; etc.; and antibodies for the above-mentioned antigens.

As antigen types, there are, besides immunoglobulin, and its modified F(ab')$_2$, Fab', Fab, and so on. They may be prepared by methods known per se in the art [see, "Immunology-1", The Nakayama Publishing Co., Ltd. (1981)]. This also applies to monoclonal antibodies.

Illustrative of the solid amorphous, spherical, polygonal, or fibrous matrix include macromolecular proteins; inorganic materials such as glass, asbestos, rock, sludge, gold, silver and alloys; synthetic resins such as polystyrene, polyethylene, silica, phenol resin, acrylic resin, cellulose, urethane resin, polyvinyl alcohol, vinyl chloride resin, polyvinylidene chloride, polypropylene, polyterephthalate, polycarbonate, nylon, fluorocarbon resin and polyester beads; and fibrous matrix such as cellulose, cotton, hemp, straw, wool, silk, glass fibers, nylon fibers, Vinylon (trade mark) fibers, acrylic fibers, polyethylene fibers and polyester fibers. The diameters of the spherical beads may preferably range from 0.05 to 0.3 mm or especially from 0.1 to 0.17 mm. On the other hand, the polygonal beads are preferably 40–300 mesh or typically 80–150 mesh. For the fibers, their diameters may preferably range from 1 micrometer to 0.3 mm or especially from 0.01–0.08 mm.

Immunoreactive reagents which are to be labelled with markers include antigens which reacts with antibodies in samples or antibodies against antigens in samples, or antigens or antibodies useful in competitive reactions with antigen or antibodies present in samples respectively. Exemplary labelling agents may embrace radioisotopes such as iodine isotopes (for example, $^{125}$I, $^{131}$I), $^{14}$C, tritium and the like; enzymes such as peroxidase, alkali phosphatase, diaphorase, $\beta$-D-galactosidase, glucose oxidase, penicillinase and so on; or fluorescent substances such as fluorescent isocyanate, fluorescent isothiocyanate, Rhodamines, etc. Methods known per se in the art may be followed to label the above-described antigens or antibodies with these labelling agents "RADIOIMMUNOASSAY, Second Series", The Kodansha Scientific Publishing Co., Ltd. (1979); J. Histo. Chem. Cytochem. 22, 1084 (1974); Immunochemistry, 6, 43 (1969); ibid., 8, 871 (1971); J. Biochem. 78, 235 (1975); "FLUORESCENT ANTIBODY METHODS", Academic Press].

Any substance may be employed as the uptaking substance so long as the substance will combine or capture below described immuno-reacted labelled substances or non-immuno-reacted labelled substances. Examples of such substance are: if the target substance is antigen, then antibody against the antigen, if the target substance is antibody, then antigen which reacts with the antibody, and substances which have affinity toward the label. In order to immobilize the capturing substance on solid matrix, either inherent adsorbancy of the uptaking substance to the solid matrix or some well established method for such purpose will be employed. Examples of such uptaking substances are: glass beads which have been treated to adsorb basic amino acids or the like, or glass beads on which cross-linking agent is coupled. Glutaraldehyde, maleimide or the like may be used as the cross-linking agent. So treated beads are then complexed with the uptaking substance for the labelled substances. Where cellulose or the like is used as matrix, the cellulose or the like is treated with an oxidizing agent such as ferrous perchromate, potassium periodate or sodium periodate causing the surface of cellulose to form aldehyde derivatives which then will form the Schiff base with amino groups of the uptaking substance resulting the immobilization of the uptaking substance to the matrix.

As one embodiment of this invention, it may be mentioned that a capillary tube is packed with labelled substance and insoluble matrix which is coupled with the uptaking substance which will immobilize the labelled substance. The tip of so manufactured capillary tube is then contacted with a sample liquid which contain target substance, thus causing the liquid to migrate upward through the inside of the capillary tube by the capillary action. As the liquid migrate upward in the capillary tube, when the target substance is similar to the labelled substance, the target substance and the labelled substance together will continue to migrate upward inside the capillary tube until the liquid encounter the uptaking substance which is immobilized on the solid matrix. At the time of the encounter, the target substance and the labelled substance will be captured by the uptaking substance on the solid matrix in an amount proportional to the concentrations of the target substance and the labelled substance. The amount of the labelled substance captured by the uptaking substance will reflect the concentration of the target substance in the sample liquid. As another embodiment of this invention, it may also be mentioned that a capillary tube is packed with a labelled substance which reacts with the target substance and with the insoluble matrix on which the uptaking substance which will immobilize the target substance is complexed. The tip of so manufactured capillary tube is then contacted with a sample liquid which contain target substance, thus causing the liquid to migrate upward through the inside of the capillary tube by the capillary action. As the liquid migrate upward in the capillary tube, when the target substance is reactive with the labelled substance, the target substance will form complex and the complex as well as unreacted target substance, unreacted labelled substance and other unreactive substances contained in the sample liquid continue to migrate upward together inside of the capillary tube until the liquid encounter the uptaking substance for the target substance which was immobilized on the solid matrix. At the time of the encounter, the unreacted target substance and the labelled substance which is in the complex with the target substance will be captured by the capturing agent on the solid matrix in an amount proportional to the concentrations of the unreacted target substance and the labelled substance which is in complex with the target substance in the liquid at the point of the encounter with the capturing agent. The amount of the labelled substance captured by the uptaking substance will reflect the concentration of the target substance in the sample liquid.

For the above method, it is necessary as needed to provide other than those mentioned above, solid particulate matrix to fill void spaces, substrate, chromogenic agent, inhibitor and the like. As the substrate and chromogenic agent, the following combinations [substrate : chromogenic agent] may be employed for their respective enzymes as label: peroxidase [hydrogen peroxide : o-dianisidine, o-tolidine, 4-chloro-1-naphthol, 2,2'-azino-e-ethylbenzothiazoline sulfonate (ABTS), 3-amino-9-ethylcarbazole, 2,7-fluorene diamine, 3-methyl-2-benzothiazolinonehydrozone (MBTH), or thyramine]; and alkali phosphatase [p-nitrophenolphosphoric acid or 4-methylunbelliferylphosphoric acid : 4-aminoantipyrine]; β-D-galactosidase [o-nitrophenol : β-D-galactoside or 4-methylumbelliferyl : β-D-glactoside]. In order to perform the above method, it is necessary some solid matrix to be co-placed with the labelled immunoreactive reagent, substrate, chromogenic agent, inhibitor and the like thereon. It is necessary then to mix the solid matrix with an aqueous or alcoholic solution of the labelled immunoreactive reagent, etc. and then to dry the resultant mixture so as to allow the reagent, etc. to adhere on the surfaces of the solid matrix.

In the present method, there are packed in a capillary tube a solid matrix with an uptaking substance immobilized thereon for its corresponding labelled substance and a solid matrix holding a labelled immunoreactive reagent thereon, and if necessary, a solid matrix bearing a substrate, chromogenic agent, inhibitor and the like, all of which matrix have been prepared in the above-described manner.

The capillary tube may be made of glass, or either transparent or translucent synthetic resin, for example, polyethylene, polycarbonate, polypropylene, polystyrene, acrylic phthalate resin or the like. The diameter of each capillary tube may preferably be 0.5-2 mm or notably 1.0-1.1 mm, while its length may preferably be 3-20 cm or particularly 5-15 cm. It is important that the inner wall of the capillary tube does not adsorb any protein thereon. It is thus preferred to treat beforehand the inner wall of the capillary tube for example with a neutral buffer solution of a protein (for instance, albumin or the like).

In order to pack the capillary tube with the solid matrix bearing the uptaking substance immobilized thereon for the labelled substance as well as with the reagent-holding solid matrix, it is necessary to close up the lower end of the capillary tube with a plug of cotton, polyester or the like, and then to establish a negative pressure within the capillary tube by means of a suction device such as aspirator, whereby sucking and packing the solid matrix in the capillary tube. It is required to pack the capillary tube with at least the solid matrix bearing the uptaking substance immobilized thereon for the labelled substance and the solid matrix holding the labelled immunoreactive reagent thereon. If necessary, the capillary tube may additionally be packed with the solid matrix holding the substrate, chromogenic agent, inhibitor and the like adhered thereon. It is necessary to pack the solid matrix with the uptaking substance immobilized thereon for the labelled substance in such a way that the sample reaches the solid matrix after the sample has been subjected to its immunoreaction. This may be achieved by packing the capillary tube with matrix bearing an uptaking substance which is capable of combining with either the immuno-reaction product with the labelled reagent or the unreacted labelled reagent so as to immobilize the labelled substance in either as the reaction product or as the unreacted immuno-reactive reagent. Alternatively one can pack a capillary tube with one matrix bearing an uptaking substance which immobilizes either the immuno-reaction product with labelled reagent or the unreacted labelled reagent and another matrix bearing an uptaking substance which immobilizes both the immuno-reaction product with labelled reagent and the unreacted labelled reagent separately at the different location in such so that the sample reaches the former first and the latter later so as to separate the immuno-reaction product with labelled reagent from that of the unreacted labelled reagent. It is also sometimes necessary to pack the solid matrix bearing the uptaking substance immobilized thereon for the labelled substance and the solid matrix holding thereon the labelled immunoreactive reagent, substrate, chromogenic agent, inhibitor and the like in such a way that they are isolated from each other. To ensure this isolation, solid matrix may be used. In the present invention, the following basic packing orders may be followed to pack an inert matrix bearing an uptaking substance immobilized thereon for a labelled substance and another inert matrix holding thereon a labelled and immuno-reactive reagent where the target component in a sample is an antigen.

(a) labelled antibody—immobilized antigen;
(b) labelled antigen—immobilized antibody;
(c) labelled antibody—immobilized antibody;
(d) labelled antibody—immobilized antibody (first)—labelled antigen—immobilized antibody (second);
(e) labelled antibody—immobilized antibody—immobilized antigen;
(f) labelled antibody—immobilized antibody—immobilized anti-label antibody;
(g) labelled antibody—(immobilized antibody+auxiliary labelled substance)—(immobilized anti-label antibody+auxiliary labelled substance); and
(h) immobilized antibody.

Besides, these capillary tubes (a)—(h) may be combined suitably.

In order to detect or quantitatively analyze a target component in a sample by using the thus-prepared measuring capillary tube, it is necessary to dip the lower end of the measuring capillary tube in a solution of the sample so as to cause the solution to be withdrawn into the capillary tube by the capillary action. Here, if the target component in the sample is an antigen, reactions such as those to be given next will take place to immobilize the labelled substance.

Capillary tube (a)

The antigen in the sample reacts first with the labelled antibody to form the antigen-labelled antibody. This antigen-labelled antibody and the remaining, unreacted labelled antibody are then caused to move up the capillary. Upon contact with the immobilized antigen, the unreacted labelled antibody reacts with the immobilized antigen, resulting in the formation of the labelled antibody-immobilized antigen to achieve immobilization.

Capillary tube (b)

The antigen in the sample is brought, along with the labelled antigen, into contact with the immobilized antibody. Both of the antigens react competitively, resulting in the immobilization of the labelled antigen as the labelled antigen-immobilized antibody.

Capillary tube (c)

The antigen in the sample reacts with the labelled antibody to form the antigen-labelled antibody. Then, the antigen-labelled antibody and the remaining, unreacted labelled antibody are caused to move, thereby contacting with the immobilized antibody. Thus, the antigen-labelled antibody reacts with the immobilized antibody, resulting in its immobilization as the immobilized antibody-antigen-labelled antibody.

Capillary tube (d)

The antigen in the sample is caused to react with the labelled antibody and form the antigen-labelled antibody, which is then brought into contact with the immobilized antibody (first) to immobilize as the immobilized antibody-antigen-labelled antibody. Also, if the antigen in the sample is present in an amount greater than the labelled antibody, the excess antigen reacts, in competition with the labelled antigen, with the immobilized antibody (second) so that it is immobilized as the labelled antigen-immobilized antibody.

Capillary tube (e)

The antigen in the sample reacts with the labelled antibody to form the antigen-labelled antibody, which in turn reacts with the immobilized antibody so that the antigen-labelled antibody is immobilized as the immobilized antibody-antigen-labelled antibody. On the other hand, any unreacted portion of the labelled antibody is caused to move further, thereby reacting with the immobilized antigen so that the unreacted fraction of the labelled antibody is immobilized as the immobilized antigen-labelled antibody.

Capillary tube (f)

The antigen in the sample reacts with the labelled antibody to form the antigen-labelled antibody, which is then brought into contact with the immobilized antibody and immobilize the antigen-labelled antibody as the immobilized antibody-antigen-labelled antibody. On the other hand, any unreacted fraction of the labelled antibody and those antigen-labelled antibody which was not immobilized by the immobilized antibody are then caused to move further so that they react with the immobilized anti-label antibody to immobilize as the immobilized anti-label antibody-labelled antibody and the immobilized anti-label antibody-labelled antibody-antigen.

Capillary tube (q)

The antigen in the sample reacts with the labelled antibody and form the antigen-labelled antibody, which is thereafter brought into contact with "the immobilized antibody+the auxiliary labelled substance," thereby immobilized as "the immobilized antibody+the auxiliary labelled substance"-antigen-labelled antibody. Furthermore, any unreacted fraction of the labelled antibody is caused to move further so that it is reacted with "the immobilized anti-label antibody+the auxiliary labelled substance", thereby resulting in its immobilization as "the immobilized anti-label antibody+auxiliary label substance" -labelled antibody. This method can detect the label only when the labelled antibody is juxtaposition to the auxiliary substance. The term "auxiliary labelled substance" as used herein means, for example, glucose oxidase which produce the substrate for peroxidase from glucose through an enzymatic reaction, NADH as co-enzyme for diaphorase, a substance which is necessary for luminescent substance to excite, or the like.

Capillary tube (h)

When a sample consisting of a mixture of the labelled substance (the labelled target substance) and the sample is soaked in, the target substance and labelled substance react, in a competitive fashion, with the immobilized antibody for their immobilization. The amount of the labelled substance is then measured. This immobilized amount decreases as the concentration of the target substance increases. A liquid, for example, a phosphate-buffered physiological saline (hereinafter abbreviated as "PBS") is then sucked into the capillary tube. The liquid is allowed to move through the capillary tube while washing the unreacted labelled substance and sample liquid away. As as result, the immobilized labelled substance and target substance are allowed to remain in the capillary tube.

When a mixture of a labelled substance (an antibody having affinity to a target substance, which has been labelled) and a sample is soaked in the capillary tube (a), a combined product of the target substance and labelled substance reacts with the immobilized antibody so as to immobilize the combined product. The amount of the thus-immobilized labelled substance increases as the concentration of the target substance increases. Then, another liquid is also soaked into the capillary tube. This second liquid passes through the capillary tube while washing any extra portion of the labelled substance and the liquid sample away. As a result, the thus-immobilized target substance is allowed to remain in the capillary tube.

In this invention, the thus-immobilized labelled substance may be measured. Where the label is a radioisotope, the amount may be determined by means of a gamma counter while holding the lower end thereof down. Alternatively, the portion of the capillary tube which contains the immobilized radio-labelled substance may be cut off for measurement. In case of the radiation cannot be measured by such a gamma counter, it is preferred to measure it by a scintillation counter. Where the labelling agent is an enzyme or fluorescent substance, the labelling agent is caused to produce a color by a substrate or color-producing agent filled in the capillary tube or by light of an exciting wavelength respectively. Thus, the amount of the labelled substance can be measured. Alternatively, the substrate and color-producing agent may be sucked after the liquid sample has been sucked in when the label is enzymes.

In the method of this invention, body fluids such as blood, serum, plasma, lymph, salivary juice and urine as well as effluent may be employed as liquid samples to be assayed. Even if a liquid sample contains one or more components inhibitory to the intended immunoreaction, its measurement may still be feasible provided that such components are in advance either inactivated, removed or diluted to such a low concentration as to avoid any deleterious effect to the measurement.

The invention will hereinafter be described by the following Examples.

EXAMPLE 1

[1]MATERIALS (1) Albumin-coated glass capillary tubes:

Through glass capillary tubes (inner diameter, 1 mm; length, 100 mm), 0.01 M phosphate-buffered saline (PBS), pH 7.2, containing 20 mg/ml bovine serum albumin (BSA) was passed. The glass capillary tubes were then aspirated to remove any remaining PBS with BSA and followed by air drying.

(2) Glass beads (GB); (diameter, 0.17 mm).

(3) Albumin-coated GB (GB.BSA).

GB were immersed in PBS containing 20 mg/ml of BSA. After washing the thus-immersed GB two to three times with distilled water, the GB were dried under vacuum.

(4) Polyester fiber:

Commercial polyester fiber was used.

(5) Dianisidine-mixed GB.BSA:

One gram of GB.BSA was mixed in 2 ml of ethanol containing 6.25 mg of o-dianisidine hydrochloride. The resultant mixture was then dried under vacuum.

(6) Peroxidase conjugated anti-rabbit IgG antibody (αRb-IgG-HRP):

Four milligrams of peroxidase were dissolved in distilled water. After adding 0.2 ml of 0.1 M sodium periodate to the solution, the contents were stirred for 20 minutes at room temperature. The reaction mixture was dialyzed overnight against 1 mM acetate buffer solution (pH 4.0). After dialysis, 0.2 M carbonate buffer solution (pH 9.5) was added to adjust the dialyzate to pH 9.5. Immediately after the pH adjustment, 1 ml of goat anti-rabbit IgG antibody (10 mg/ml) in 0.01 M carbonate buffer solution (pH 9.5) was added. The contents were stirred at room temperature for 2 hours. After completion of the reaction, the reaction mixture was mixed with 0.1 ml of sodium borohydride (4 mg/ml) and the resulting mixture was allowed to stand at 4° C. for 2 hours. Upon completion of the reaction, the reaction mixture was chromatographed through Sephacryl S-200 (a product of Farmacia AB) in a column (column diameter: 2.5 cm; column length: 30 cm) and was eluted by 0.01 M PBS. High molecular fractions which were eluted first were collected and then lyophilized for their storage.

(7) αRb-IgG-HRP mixed GB.BSA:

Eight grams of GB.BSA were added to a portion of the lyophilizate prepared in the above paragraph (6), which portion was equivalent to 1 ml of αRb-IgG-HRP. The resulting mixture was mixed uniformly in a mortar.

(8) Rabbit IgG fixed GB (Rb-IgG-O):

Five milliliters of concentrated sulfuric acid were added to 5 g of GB. The resultant mixture were allowed to stand at room temperature for 5 minutes. It was then washed with distilled water until the washings became neutral. The thus-washed GB were coated with 1 ml of poly-L-lysine (30 mg/ml), followed by stirring of the resultant mixture at room temperature for 1 hour and washed with distilled water. Subsequent to the washing, the poly-L-lysine coated GB was mixed with 2 ml of 2.5% glutaraldehyde in PBS. The resultant mixture was stirred at room temperature for 1 hour. After washing the reaction mixture with distilled water, 2 ml of rabbit IgG (5 mg/ml) was added. The thus-prepared mixture was stirred at room temperature for 3.5 hours, followed by several washing with PBS and was dried under vacuum.

[2]Preparation of Capillary Tubes for Measurements

Five marks were respectively placed, first one at a point 5 mm from the lower end of the albumin-coated glass capillary tubes and then successive four marks upward on the capillary tube with an interval of 3.5 mm. Polyester fibers (a-1) were packed over the first 5 mm. The lower end was then connected to a vacuum pump to produce a negative pressure within the capillary tube so that the dianisidine-mixed GB.BSA (a-2) was sucked to fill up the next 3.5 mm. In the same manner, the GB.BSA (a-3), αRb-IgG-HRP mixed GB.BSA (a-4), GB.BSA (a-5) and Rb-IgG-O (a-6) were packed successively. The GB (a-7) was then packed through the remaining space of the capillary tube to a point 5 mm the way down from the upper end. Finally, polyester fibers were packed in the remaining 5 mm. (FIG. 1)

[3-1] Distinction Between Human Serum and Rabbit Serum

Two capillary tubes were provided for detection. The lower end of one of the capillary tubes was dipped in human serum, while that of the other capillary tube was dipped in rabbit serum. Each serum was allowed to soak up to a zone indicated by (a-6) in FIG. 1. At this stage, the amount of the soaked serum was about 8 μl. It took 1 minute for the soaking. Each of the capillary tube was then dipped at its lower end in PBS containing 0.003% of hydrogen peroxide, which was then allowed to soaked up to a point near the upper end of the capillary tube (8–9 cm the way up from the lower end). It took 15 minutes for this soaking. As a result, the Rb-IgG-O zone [(a-6) in FIG. 1] was colored in brown in the case of human serum. However, no color was observed in the case of rabbit serum.

[3-2] Distinction Between Human Blood and Rabbit Blood, both containing an anticoagulant (EDTA)

The procedures of [3-1] were followed except that PBS containing 0.03% of hydrogen peroxide was used as a substrate solution. As a result, the zone corresponding to the Rb-IgG-O was colored in brown in the case of human blood, while no color was observed in the case of rabbit blood.

EXAMPLE 2

[1] MATERIALS (1) Albumin-coated glass capillary tubes:
Albumin-coated glass capillary tubes were prepared in the same manner as in Example 1, [1], (1) except that glass capillary tubes with 1.5 mm diameter and 125 mm long were used.

(2) Glass beads (GB) (diameter: 0.17 mm)

(3) Albumin-coated GB (GB.BSA):
Were used the same albumin-coated GB as those referred to in Example 1, [1], (3).

(4) Polyester fiber (5) Dianisidine-mixed GB.BSA:
Were used the same dianisidine-mixed GB.BSA as those referred to in Example 1, [1], (5).

(6) Peroxidase conjugated rabbit IgG (Rb-IgG-HRP):
Prepared in the same manner as in Example 1, 1], (6) except that goat anti-rabbit IgG antibody was replaced by rabbit IgG.

(7) Rb-IgG-HRP mixed GB.BSA:
Sixteen grams of GB.BSA were added to a portion of the lyophilizate prepared in (6), which portion is equivalent to 1 ml of Rb-IgG-HRP. The resultant mixture was uniformly mixed in a mortar.

(8) Anti-rabbit IgG antibody fixed GB (αRb-IgG-O):
The procedures of Example 1, [1], (8) were followed except that goat anti-rabbit IgG antibody was used in lieu of the rabbit IgG.

(9) Plunger with a hole:
A hole was formed in an upper part of a rubber suction cup of dimensions conforming with the capillary tube.

(10) Heparin and EDTA mixed GB.BSA:
Mixed uniformly in a mortar were 10 mg of heparin, 1.15 g of EDTA 2K and 8.84 g of GB.BSA. A 0.2 g portion of the resultant mixture was taken out, to which 9.8 g of GB.BSA was further added. The thusobtained mixture was stirred evenly in the same manner.

2] Preparation of Capillary Tubes for Measurements

The procedures of Example 1, [2] were followed to prepare the following capillary tubes.

Polyester fibers (b-1) were packed over the first 5 mm, heparin and EDTA mixed GB.BSA (b-2) over the next 3.5 mm, the dianisidine-mixed GB.BSA (b-3) over the next 3.5 mm, and similarly, the GB.BSA (b-4), Rb-IgG-HRP mixed GB.BSA (b-5), GB.BSA (b-6) and αRb-IgG-O(b-7) were respectively packed 3.5 mm each. The GB (b-8) was then packed in the remaining space of the capillary tube up to a point 5 mm the way down from the upper end of the capillary tube, and the remaining 5 mm was packed with polyester fibers. (FIG. 2)

3] Distinction Between Fresh Human and Rabbit Bloods

Two capillary tubes were provided, and rubber suction cups, each with a hole, were attached respectively to the upper ends of the capillary tubes. The lower end of one of the capillary tubes was brought into contact with a nick produced in a part of human ear, while the lower end of the other capillary tube was brought into contact with a nick produced in a part of rabbit ear. Each fresh blood was slowly sucked to the zone (b-7) in FIG. 2, while making use of the rubber suction cup. At this stage, the amount of the sucked blood was about 15 μl. It took 20 seconds for the suction. Then, the lower end of each of the capillary tubes was dipped in PBS containing 0.003% of hydrogen peroxide. The PBS containing 0.003% of hydrogen peroxide was sucked, making use of the rubber suction cup, to a point near the upper end (9–10 cm the way up from the lower end) of the capillary tube. It took 7 minutes for the suction. As a result, the zone corresponding to the anti-Rb-IgG [(b-7) in FIG. 2] was colored in brown in the case of human blood but in the case of rabbit blood, the same zone was tinged lightly compared with the former.

EXAMPLE 3 [1] Materials:

(1) Albumin-coated glass capillary tubes:
The albumin-coated glass capillary tubes of Example 1, [1]. (1) were used.

(2) Glass beads (GB; diameter: 0.1 mm)

(3) Albumin-coated GB (GB.BSA):
GB.BSA were prepared in the same manner as in Example 1, [1], (3) except that 0.1-mm glass beads were used instead of the 0.17-mm glass beads.

(4) Absorbent cotton (5) Peroxidase conjugated anti-C-reactive protein antibody (αCRP-HRP):
Prepared in the same manner as in Example 1, [1], (6) except that goat anti-CRP antibody was substituted for goat anti-rabbit IgG antibody.

(6) αCRP-HRP mixed GB.BSA:
Eight grams of GB.BSA (3) were added to a portion of the lyophilizate prepared in (5), which portion was equivalent to 1 ml of αCRP-HRP. The resulting mixture was evenly mixed in a mortar.

(7) αCRP antibody fixed GB (αCRP-O):
Prepared in the same manner as in Example 1, [1], (8) except that goat αCRP antibody was used in place of the rabbit IgG, and the glass beads in [1], (2) of this Example was used.

(8) Color-producing substrate solution:
PBS containing 0.03% of hydrogen peroxide, 0.25% of gelatin and 0.03% of o-tolidine.

2] Preparation of Capillary Tubes for Measurements

The following capillary tubes were prepared by following the procedures of Example 1, [2]. The absorbent cotton (c-1) was packed over the first 5 mm, and GB.BSA (c-2), αCRP-HRP mixed GB.BSA (c-3), GB.BSA (c-4) and αCRP-O (c-5) were then packed respectively 5 mm each. The GB (c-6) was packed in the remaining space of the capillary tube up to a point 5 mm the way down from the upper end of the capillary tube, and the absorbent cotton was packed in the remaining 5 mm. (FIG. 3)

3] Determination of the presence or absence of CRP

Four capillary tubes were provided for detection of CRP. Their lower ends were respectively dipped in (I) rabbit serum, (II) normal human serum, (III) patient serum, and (IV) serum containing 5 mg/dl of CRP. The liquid samples were each soaked up to the zone (c-3) in FIG. 3. Here, the amount of each of the thus-soaked samples was about 5 μl. It took 30–60 seconds for the soaking.

Thereafter, the lower ends of the capillary tubes were dipped in a color-producing substrate solution. The color-producing substrate solution was soaked up to a point (8–9 cm the way up from the lower end) near the upper end of each capillary tube. It took minutes for the soaking. As a result, no color was observed in the zone corresponding to the αCRP-O [(c-5) in FIG. 3] in the case of (I) and (II), while a greenish color was observed in the same zone in the case of (III) and (IV).

EXAMPLE 4

Materials (1) Albumin-coated glass capillary tubes:
The albumin-coated glass capillary tubes of Example 1, [1], (1) were used.

(2) Glass beads (GB; diameters: 0.1 mm)

(3) Albumin-coated GB (GB.BSA):
The albumin-coated GB of Example 3, [1], (3) were used.

(4) Dianisidine-mixed GB.BSA:
Prepared in the same manner as in Example 1, (5) except that 0.1-mm glass beads were used in place of the 0.17-mm glass beads.

(5) Glucose oxidase conjugated absorbent cotton (GOD-O):
Provided were 780 mg of the absorbent cotton and 214 mg of sodium periodate, to which 40 ml of distilled water was added. The resultant mixture was stirred at room temperature for 1 hour. After the reaction, the reaction mixture was washed thoroughly with distilled water, followed by an addition of 10 mg of glucose oxidase. After mixing them at room temperature for 3 hours, the resulting mixture was washed thoroughly with distilled water and was then dried under vacuum.

(6) Glucose mixed absorbent cotton (Glu-mixed absorbent cotton):
Provided was 1 g of the absorbent cotton, followed by its mixing with 100 mg of glucose. Thereafter, 2 ml of distilled water was added and the resultant mixture was stirred well to dissolve the glucose. Then, the absorbent cotton was dried under vacuum.

(7) Peroxidase conjugated anti-fibrin degradation products (αFDP-HRP):
Prepared in the same manner as in Example 1, (6) except that goat anti-rabbit IgG antibody was replaced by mouse anti-FDP antibody (monoclonal antibody-1).

(8) αFDP-HRP mixed GB.BSA:
Eight grams of the GB.BSA (3) were added to a portion of the lyophilizate prepared in (7), which portion was equivalent to 1 ml of the αFDP-HRP. The resultant mixture was evenly stirred in a mortar.

(9) αFDP-fixed GB (αFDP-O):
Prepared in the same manner as in Example 1, (8) except that the rabbit IgG was replaced by mouse αFDP antibody (monoclonal antibody-2).

(10) Glutathione-mixed GB.BSA:
Ten milligrams of glutathione and 5 g of GB.BSA were uniformly mixed in a mortar.

(11) Absorbent cotton

[2] Preparation of Capillary Tubes for Detection

From the lower end of each albumin-coated glass capillary tube, the first mark was made at 5 mm and the second at 10 mm from the lower end. Then, six marks each with an interval of 3.5 mm were made. Two fibrous reagents were inserted from the lower end. Namely, the GOD-O (d-2) was first packed from a point 5 mm the way up from the lower end to a point 10 mm the way up from the same lower end, and the Glu-mixed absorbent cotton (d-1) was then packed from the lower end to the point 5 mm the way up from the lower end, both using a needle. Thereafter, while sucking from the lower end, there were packed, each over a 3.5-mm length, the dianisidine-mixed GB.BSA (d-3), GB.BSA (d-4), glutathione-mixed GB.BSA (d-5), αFDP-HRP mixed GB.BSA (d-6), GB.BSA (d-7) and αFDP-O (d-8) respectively. The GB (d-9) was then packed in the remaining space of the capillary tube up to a point 5 mm the way down from the upper end of the capillary tube, and the absorbent cotton was packed over the remaining 5 mm. (FIG. 4)

[3] DETECTION OF FDP IN URINE

Two capillary tubes were provided for detection. One of the capillary tubes was dipped in urine containing FDP ($D_2$) in an amount of 50 μg per milliliter of the urine, while the other capillary tube was dipped in normal human urine. Both urine samples were soaked up to points near the upper ends (8–9 cm the way up from the lower ends) of their corresponding capillary tubes. Here, the amount of each of the soaked urine samples was about 25 μl. It took 9 minutes for the soaking. As a result, the zone corresponding to the αFDP-O [(d-8) in FIG. 4] was colored in brown in the case of the FDP-added urine. No color was however observed in the case of the normal human urine.

EXAMPLE 5

[1] Materials (1) Albumin-coated glass capillary tubes:
The albumin-coated glass capillary tubes of Example 1, [1], (1) were used.

(2) Glass beads (GB; diameter: 0.17 mm)

(3) Albumin-coated GB (GB.BSA): The GB.BSA of Example 3, [1], (3) were used.

(4) Polyester fiber (5) Dianisidine-mixed GB.BSA:
The dianisidine-mixed GB.BSA of Example 1, [1], (5) were used.

(6) Peroxidase conjugated rabbit IgG antibody (Rb-IgG-HRP):

The Rb-IgG-HRP of Example 2, [2], (6) was used.

(7) Rb-IgG-HRP mixed GB.BSA:

The Rb-IgG-HRP mixed GB.BSA, of Example 2, [1], (7), was used.

(8) Rabbit IgG fixed GB (Rb-IgG-O):

The Rb-IgG-O of Example 1, [1], (8) was used.

[2] PREPARATION OF CAPILLARY TUBES FOR DETECTION

Following the procedures of Example 1, [2], the following capillary tubes were prepared. The polyester fibers (e-1) were packed over the first 5 mm, followed by packing of the dianisidine-mixed GB.BSA (e-2), GB.BSA (e-3), Rb-IgG-HRP mixed B.BSA (e-4), GB.BSA (e-5) and Rb-IgG-O (e-6) respectively over 3.5 mm by 3.5 mm. The GB (e-7) was thereafter packed in the remaining space in the capillary tube up to a point 5 mm the way down from the upper end of the capillary tube, and the polyester fibers were finally packed in the remaining 5 mm. (FIG. 5)

[3] Determination of the Presence or Absence of anti-Rb-IgG antibody

Two capillary tubes were provided for detection. The lower ends of the capillary tubes were dipped respectively in goat serum under immunization with Rb-IgG (I) and normal goat serum (II) (confirmed by the Ouchterlony method). The samples were soaked up to points (e-3) in FIG. 5. At this stage, the amount of each of the samples was about 3 $\mu$. It took 20 seconds.

Then, the lower ends of the capillary tubes were dipped in PBS which contained 0.03% of hydrogen peroxide. The PBS containing 0.03% of hydrogen peroxide was soaked up to points near the upper ends (8-9 cm the way down from the lower ends) of the capillary tubes. It took 20 minutes for the soaking. As a result, the zone corresponding to the Rb-IgG-O [(e-6) in FIG. 5 was colored in brown in the case of the goat serum containing anti-Rb-IgG antibody (I), while no color was observed in the case of the normal goat serum (II).

EXAMPLE 6

[1]Materials:

(1) Albumin-coated glass capillary tubes:

The albumin-coated glass capillary tubes of Example 1, [1], (1) were employed.

(2) Albumin-coated glass beads (GB.BSA):

The GB.BSA of Example 3, [1], (1) were used.

(3) Absorbent cotton (4) Peroxidase conjugated anti-human serum albumin antibody ($\alpha$HSA-HRP):

Prepared in the same manner as the $\alpha$Rb-IgG-HRP of Example 1, [1], (6) except that goat anti-rabbit IgG antibody was replaced by rabbit anti-human serum albumin antibody.

(5) $\alpha$HSA-HRP mixed GB.BSA: Prepared in the same manner as in Example 3, [1], (6) except that the $\alpha$-HSA-HRP (4) of this Example was employed in lieu of the $\alpha$CRP-HRP. (6) $\alpha$HSA antibody fixed GB ($\alpha$HSA-O):

Prepared in the same manner as in Example 3, (7) except that the goat $\alpha$CRP antibody was replaced by rabbit $\alpha$-HSA antibody. (7) Color-producing substrate solution:

0.01-M Phosphate buffered saline containing 0.03% of hydrogen peroxide, 0.25% of gelatin and 0.03% of 2,2'-azinodi(3-ethylbenz-thiazoline)-6-sulfonic acid.

[2]Preparation of Capillary Tubes for Detection

The following capillary tubes were prepared in the same manner as in Example 1, [2].

The absorbent cotton (f-1) was packed over the first 5 mm, and then the GB.BSA (f-2) over next 7 mm, the $\alpha$HSA-HRP mixed GB.BSA (f-3) over 3.5 mm, the GB.BSA (f-4) over 7 mm, and the $\alpha$HSA-O (f-5) over 3.5 mm. The GB.BSA (f-6) was thereafter packed in the remaining space of the capillary tube up to a point 5 mm the way down from the upper end of the capillary tube, and the absorbent cotton was also packed in the remaining 5 mm. After completion of the packing, a mark was placed at a point 5 cm the way up from the lower end. (FIG. 6)

[3] Determination of the presence or absence of human albumin in effluent

Three testing tubes were provided for detection. The lower ends of the testing tubes were dipped respectively in PBS containing human serum in an amount of 1 ml per liter of the PBS (I), Effluent 1 (II) and Effluent 2 (III). These samples were soaked up to the zones (f-5) in FIG. 6. At this stage, the amount of each of the soaked samples was about 9 $\mu$1. It took 1 minute tor the soaking. Tnereafter, the lower ends of the capillary tubes were dipped in a color-producing substrate solution. The color-producing substrate solution was soaked up to points about 5 cm up from the lower ends of the capillary tubes. It took 15 minutes for the soaking. As a result, in the case of (I) and (II), blue color were observed respectively in the zones corresponding to the $\alpha$HSA-O [(f-5) in FIG. 6], whereas no color was observed in the case of (III). From these results, it was able to determine that Effluent 1 contained human albumin.

EXAMPLE 7

[1] Material (1) Albumin-coated glass capillary tubes:

The albumin-coated glass capillary tubes of Example 1, [1], (1) were employed.

(2) Glass beads (GB; diameter: 0.1 mm)

(3) Albumin-coated GB (GB.BSA): The GB.BSA of Example 3, [1], (3) were used.

(4) Polyester fiber (5) Dianisidine-mixed GB.BSA:

The dianisidine-mixed GB.BSA of Example 4, (4) were used.

(6) Peroxidase conjugated anti-$\alpha$-fetoprotein antibody (monoclonal antibody: produced by us) $\alpha$AFP-HRP):

Prepared in the same manner as in Example 1, (6) except that goat anti-rabbit IgG antibody was replaced by mouse anti-$\alpha$-fetoprotein antibody (monoclonal antibody-1).

(7) $\alpha$AFP-HRP mixed GB.BSA:

Prepared in the same manner as in Example 3, (6) except that the $\alpha$CRP-HRP was replaced by the $\alpha$AFP-HRP (6) of this Example.

(8) Anti-$\alpha$-fetoprotein antibody fixed GB ($\alpha$AFP-O):

Prepared in the same manner as in Example 3, [1], (7) except that goat $\alpha$CRP antibody was replaced by mouse anti-α-fetoprotein antibody (monoclonal antibody-2; produced by us).

(9) α-Fetoprotein fixed GB (AFP-O):

Prepared in the same manner as in Example 3, [1], (7) except that goat αCRP antibody was replaced by α-fetoprotein (product of The Green Cross Corp.).

[2] Preparation of capillary tubes for measurements

The following capillary tubes were prepared in the same manner as in Example 1, [2].

The polyester fibers (g-1) were packed over the first 5 mm, followed by packing of the dianisidine-mixed GB.BSA (g-2), GB.BSA (g-3), αAFP-HRP mixed GB.BSA (g-4), GB.BSA (g-5), αAFP-O (g-6), GB.BSA (g-7) and AFP-O (g-8) respectively 3.5 mm each. Then, the GB (g-9) was packed in the remaining space of the capillary tube to a point 5 mm the way down from the upper end thereof, and the polyester fibers were again packed in the remaining 5 mm. (FIG. 7)

[3] Measurement of α-fetoprotein in serum

Six capillary tubes were provided for measurements. The lower ends of the capillary tubes were dipped respectively in serum containing α-fetoprotein in an amount of 0 g per milliliter of the serum (I), serum containing α-fetoprotein in an amount of 100 ng per milliliter of the serum (II), serum containing α-fetoprotein in an amount of 1 μg per milliliter of the serum (III), serum containing α-feto-protein in an amount of 10 μg per milliliter of the serum (IV), normal human serum (V), and patient serum (VI). These samples were soaked up to the zones (g-8) in FIG. 7. The amount of each of the soaked samples was about 10 μ. It took 2 minutes for the soaking. Thereafter, the lower ends of the capillary tubes were dipped in PBS which contained 0.003% of hydrogen peroxide. The PBS containing 0.003% of hydrogen peroxide was soaked up to points near the upper ends (8–9 cm the way up from the lower ends) of the capillary tubes. It took 25 minutes for the soaking. As a result, the sample (I) gave no color to the αAFP-O [(g-6) in FIG. 7] but left a dark color at the AFP-O [(g-8) in FIG. 7]. The sample (II) lightly tinged the αAFP-O [(g-6) in FIG. 7] and dark colored the AFP-O [(g-8) in FIG. 7]. The sample (III) colored not only αAFP-O [(g-6) in FIG. 7] but also the AFP-O [(g-8) in FIG. 7]. In the case of the sample (IV), the αAFP-O [(g-6) in FIG. 7] was dark colored and the AFP-O [(g-8) in FIG. 7] was lightly tinged. The samples (V) and (I) gave the same results, while the samples (VI) and (II) provided the same results. From the above results, no α-fetoprotein was observed in the normal human serum, whereas it was detected in the patient serum which contained α-fetoprotein in an amount of about 100 ng per milliliter of the serum.

EXAMPLE 8

[1] Materials (1) Albumin-coated glass capillary tubes:

The albumin-coated glass capillary tubes of Example 1, [1], (1) were employed.

(2) GB (diameter: 0.17 mm)

(3) GB.BSA:

The GB.BSA of Example 1, [1], (3) were employed.

(4) Polyester fiber:

(5) Dianisidine-mixed GB.BSA:

The dianisidine-mixed GB.BSA of Example 1, [1], (5) were used.

(6) Sodium perborate mixed GB.BSA:

Twelve milligrams of sodium perborate and 10 g of GB.BSA were mixed evenly in a mortar.

(7) Glutathione-mixed GB.BSA:

Forty milligrams of glutathione and 10 g of GB.BSA were mixed evenly in a mortar. (8) Peroxidase conjugated with anti-fibrin degradation product antibody (monoclonal antibody-1) (αFDP-HRP):

Prepared in the same manner as in Example 1, [1], (6) except that the goat anti-rabbit IgG antibody was replaced by mouse anti-fibrin degradation product antibody (monoclonal antibody-1, produced by us).

(9) αFDP-HRP mixed GB.BSA:

Prepared in the same manner as in Example 1, [1], (7) except that the α-Rb IgG-HRP was replaced by αFDP-HRP.

(10) α-FDP antibody fixed GB (αFDP-O):

Prepared in the same manner as in Example 1, [1], (8) except for the substitution of mouse antifibrin degradation product antibody (monoclonal antibody-2 produced by us) for the Rb-IgG. (11) FDP-fixed GB(FDP-O):

Prepared in the same manner as in Example 1, [1], (8) except that the Rb-IgG was replaced by FDP.

(12) Albumin-mixed GB.BSA:

Twenty milligrams of bovine serum albumin and 1 g of GB.BSA were evenly mixed in a mortar. [2] Preparation of capillary tubes for measurements:

The following capillary tubes were prepared in the same manner as in Example 1, [2].

The polyester fibers (h-1) were packed over the first 5 mm, followed by the packing of the albumin-mixed GB.BSA (h-2), dianisidine-mixed GB.BSA (h-3), sodium perborate mixed GB.BSA (h-4), glutathione-mixed GB.BSA (h-5), GB.BSA (h-6), αFDP-HRP mixed GB.BSA (h-7), GB.BSA (h-8), αFDP-O (h-9), GB.BSA (h-10) and FDP-O (h-11) respectively 3.5 mm each. Thereafter, the GB (h-12) was packed in the remaining space of the capillary tube up to a point 5 mm the way down from the upper end of the capillary tube, and the polyester fibers were packed in the remaining 5 mm. (FIG. 8)

[3] Detection of FDP in urine

Four capillary tubes were provided for detection. The lower ends of the capillary tubes were dipped respectively in normal urine (I), urine added with FDP in an amount of 50 μg per milliliter of the urine (II), urine added with FDP in an amount of 1 mg per milliliter of the urine (III) and patient urine (IV). These samples were soaked up to points near the upper ends (8–9 cm the way up from the lower ends) of their corresponding capillary tubes. The amount of each of the thus-soaked urine samples was about 25 μl. It took 20 minutes for the soaking. As a result, the urine sample (I) did not color the αFDP-O [(h-9) in FIG. 8] but gave a dark color at the FDP-O [(h-11) in FIG. 8]. The urine sample (II) gave a brown color not only to the αFDP-O [(h-9) in FIG. 8] but also to FDP-O [(h-11) in FIG. 8]. In the case of the urine sample (III), a dark color was observed at the αFDP-O [(h-9) in FIG. 8] and a light tinge was also observed at the FDP-O [(h-11) in FIG. 8]. In the case of the urine sample (IV), it was able to determine, in view of the results obtained with respect to the urine sample (II), that the urine sample (IV) contained FDP in an amount of about 50 μg per milliliter of the urine sample.

EXAMPLE 9

[1] Materials (1) Albumin-coated capillary tubes:

The albumin-coated capillary tubes of Example 1, [1], (1) were used.

(2) Glass beads (GB; diameter: 0.17 mm)

(3) Albumin-coated glass beads (GB.BSA):

The albumin-coated GB of Example 1, [1], (3) were used.

(4) Polyester fiber (5) Dianisidine-mixed GB.BSA:

The dianisidine-mixed GB.BSA of Example 1, [1], (5) were used.

(6) Peroxidase conjugated anti-α-fetoprotein antibody (αAFP-HRP):

The peroxidase conjugated anti-α-fetoprotein antibody, of Example 7, [1], (6), was used.

(7) αAFP-HRP mixed GB.BSA:

Prepared in the same manner as in Example 1, [1], (7) except that the αRb-IgG-HRP was replaced by αAFP-HRP.

(8) Anti-α-fetoprotein antibody fixed GB (αAFP-O):

Prepared in the same manner as in Example 1, [1], (8) except for the replacement of the rabbit IgG with anti-α-fetoprotein antibody.

(9) Anti-peroxidase antibody fixed GB (αHRP-O):

Prepared in the same manner as in Example 1, [1], (8) except that the rabbit IgG was replaced by goat anti-peroxidase antibody.

[2] Preparation of capillary tubes for measurements:

Following the procedures of Example 1, [2], the following capillary tubes were prepared.

The polyester fibers (i-1) were packed over the first 5 mm, followed by the packing of the dianisidine-mixed GB.BSA (i-2), GB.BSA (i-3), αAFP-HRP mixed GB.BSA (i-4), GB.BSA (i-5), αAFP-O (i-6), GB.BSA (i-7) and αHRP-O(i-8) respectively 3.5 mm each. Thereafter, the GB (i-9) were packed in the remaining space of the capillary tube up to a point 5 mm the way down from the upper end of the capillary tube, and the polyester fibers were packed in the remaining 5 mm. (FIG. 9)

[3] Detection of α-fetoprotein in serum

Three capillary tubes were provided for detection. The lower ends of the capillary tubes were dipped respectively in serum containing α-fetoprotein in an amount of 0 g per milliliter of the serum (I), serum containing α-fetoprotein in an amount of 500 ng per milliliter of the serum (II), and serum containing α-fetoprotein in an amount of 10 μg per milliliter of the serum (III). The serum samples were soaked up to the zones (i-8) in FIG. 9. The amount of each of the thus-soaked serum samples was about 10 μl. It took 1 minute for the soaking. Thereafter, the lower ends of the capillary tubes were dipped in PBS containing 0.003% of hydrogen peroxide to soak it to points near the upper ends (8–9 cm the way up from the lower ends) of the capillary tubes. It took 20 minutes for the soaking. As a result, the serum sample (I) gave no color to the αAFP-O [(i-6) in FIG. 9] but produced an intense brown color at the αHRP-O [(i-8) in FIG. 9]. The serum sample (II) colored not only the αAFP-O [(i-6) in FIG. 9] but also the αHRP-O [(i-8) in FIG. 9]. The serum sample (III) deeply colored the αAFP-O [(i-6) in FIG. 9]and also colored the αHRP-O [(i-8) in FIG. 9]. From the above results, the concentrations of α-fetoprotein were distinguished from one another from the colors of the zones (i-6) and (i-8) in FIG. 9.

Example 10

[1] Materials:

(1) Albumin-coated glass capillary tubes:

The albumin-coated glass capillary tubes of Example 1, [1], (1) were used.

(2) Glass beads (GB; diameter: 0.1 mm)

(3) Albumin-coated GB (GB.BSA):

The GB.BSA of Example 3, [1], (1) were employed.

(4) Polyester fiber (5) Dianisidine-mixed GB.BSA:

The dianisidine-mixed GB.BSA of Example 4, [1], (4) were used.

(6) Peroxidase conjugated anti-α-fetoprotein antibody (monoclonal antibody-1; produced by us; Fab') αAFP-HRP):

Dropped with stirring were 1.5 ml of 0.1M phosphate buffer solution (pH 7.0) containing 10 mg of peroxidase and 0.2 ml of dimethylsulfoxide solution containing 16 mg of N-succinimidyl-4-(N-maleimidomethyl)cyclohexane-1-carbonate (SMCC). They were mixed and reacted at 30° C. for 1 hour. The reaction mixture was centrifuged (at 3000 rpm and for 10 minutes) and the precipitated excess reagent was removed. Maleimidized-peroxidase was separated by gel chromatography (Sephadex G-25; 0.1M phosphate buffer solution, pH 6.0). On the side, the F(ab')$_2$ was prepared in a manner known per se in the art. Mercaptoethylamine hydrochloride was then added to 0.1 M phosphate buffer solution (pH 6.0) containing purified F(ab')$_2$ (derived from monoclonal antibody-1; produced by us) in an amount of 10 mg per milliliter of the buffer solution until the final concentration of the mercaptoethylamine hydrochloride reached 0.01M. The contents were reacted at 37° C. for 90 minutes. The reaction mixture was subjected to gel chromatography using Sephadex G-25 and 0.1M phosphate buffer solution containing 5 mM of EDTA as the elute to separate the Fab'. Enzyme-conjugated Fab' was subjected to gel chromatography using "Ultrogel ACA-44" (product of LKB) and 0.1M phosphate buffer solution (pH 6.5) as the elute. The thus-separated and purified products were lyophilized.

(7) αAFP-HRP mixed GB.BSA:

Prepared in the same manner as in Example 3, [1],(6) except that the αCRP-HRP was replaced by α-AFP-HRP.

(8) Anti-α-fetoprotein antibody fixed GB (αAFP-O):

The αAFP-O of Example 7, [1], (8) was used.

(9) Glucose oxidase polymerized with albumin beads mixed GB.BSA (GOD-O):

One hundred milligrams of glucose oxidase and 400 mg of bovine serum albumin were provided. They were dissolved in 5 ml of 0.02M acetate buffer solution (pH 5.0), followed by an addition of 2 ml of 2.5% glutaraldehyde. The resultant mixture was gently stirred and was then allowed to stand for 1 hour. After that, it was coagulated and was thereafter centrifuged to collect the precipitate. The thus-collected precipitate was added with 20 ml of 0.1M lysine. The resulting mixture was allowed to stand overnight. It was then washed with distilled water and the precipitate was collected. It was dried for use. Seven milligrams of the thus-obtained product and 1 g of GB.BSA were uniformly mixed.

(10) Glutathione-mixed GB.BSA:

The glutathione-mixed GB.BSA of Example 4, [1], (10) were employed.

(11) PBS containing glucose in an amount of 1 mg per milliliter of the PBS

[2] Preparation of capillary tubes for measurements

Following the procedures of Example 1, [2], the following capillary tubes were prepared.

Figure 10:

The polyester fibers (j-1) were packed over the first 5 mm, followed by the packing of dianisidine-mixed GB.BSA (j-2), GB.BSA (j-3), αAFP-HRP mixed GB.BSA (j-4), glutathione-mixed GB.BSA (j-5), GOD-O (j-6) and αAFP-O (j-7) respectively 3.5 mm each. Thereafter, the GB (j-8) were packed in the remaining space of the capillary tube to a point 5 mm from the upper end of the capillary tube, and the polyester fibers were also packed over the remaining 5 mm. (FIG. 10)

[3] Detection of α-fetoprotein in serum

Three capillary tubes were provided for detection. Their lower ends were dipped respectively in serum containing α-fetoprotein in an amount of 0 g per milliliter of the serum (I), serum containing α-fetoprotein in an amount of 500 ng per milliliter of the serum (II), and serum containing α-fetoprotein in an amount of 10 μg per milliliter of the serum. The serum samples were soaked up to the zones (j-7) in FIG. 10. The amount of each of the thus-soaked serum samples was about 9 μl. It took 2 minutes for the soaking. Thereafter, the lower ends of the capillary tubes were dipped in PBS which contained glucose in an amount of 1 mg per milliliter of the PBS. The glucose-containing PBS was soaked up to points near the upper ends (8–9 cm the way up from the lower ends) of the capillary tubes. It took 25 minutes for the soaking. As a result, the serum sample (I) gave no color to the αAFP-O[(j-7) in FIG. 10]. In the case of the serum sample (II), the αAFP-O [(j-7) in FIG. 10] was colored. The serum sample (III) colored deeply the αAFP-O [(j-7) in FIG. 10]. From the above results, it was able to distinguish the concentrations of α-fetoprotein from one another.

EXAMPLE 11

[1] Reagents (1) Albumin-coated capillary tubes:
The albumin-coated capillary tubes of Example 2, [1], (1) were used.

(2) Glass beads (GB; diameters: 0.17 mm)

(3) Albumin-coated glass beads (GB.BSA):
The GB.BSA of Example 1, [1], (3) were used.

(4) Absorbent cotton (5) Fluorescine isothiocyanate labelled anti-rabbit IgG antibody (αRb-IgG-FITC):
To 5 mg of goat anti-rabbit IgG antibody in 1 ml of saline, 0.1 ml of 0.5-M carbonate-buffered saline (pH 9.5) was added to dissolve the antibody. 0.05-M carbonate-buffered saline (pH 9.5) containing FITC in an amount of 2 mg per milliliter of the saline, which had been prepared on the side, was placed in a 20-ml beaker. The IgG solution was placed in a dialysis tubing and the tubing was then immersed in the FITC solution. They were reacted to each other at 4° C. overnight. After the reaction, the contents of the dialysis tubing was subjected to gel chromatography (Sephacryl S-200; solution: 0.01 M phosphate-buffered saline) to separate the resultant fluorescine-labelled compound. The thus-purified and separated compound was lyophilized.

(6) αRb-IgG-FITC mixed GB.BSA:
Two grams of GB.BSA were added to a portion of the lyophilizate prepared in the above step (5), which portion was equivalent to 1 ml of αRb-IgG-FITC. The resultant mixture was evenly stirred in a mortar.

(7) Rb-IgG fixed GB (Rb-IgG-O):
The Rb-IgG-O of Example 1, [1], (8) was used. [2] Preparation of capillary tubes for measurements:

The following tubes were prepared in the same manner as in Example 1, [2].

Figure 11:
Figure 12:
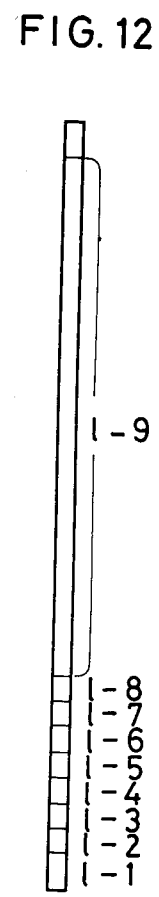

The absorbent cotton (k-1) was packed over the first 5 mm, followed by the packing of the GB.BSA (k-2) 5 over the next 3.5 mm. Thereafter, the αRb-IgG-FITC mixed GB.BSA (k-3), GB.BSA (k-4) and Rb-IgG-O (k-5) were similarly packed respectively 3.5 mm each. Then, the GB.BSA (k-6) was packed in the remaining space of the capillary tube up to a point 5 mm the way down from the upper end of the capillary tube, and the absorbent cotton was packed over the remaining 5 mm. (FIG. 11)

[3] Distinction between human serum and rabbit serum

Two capillary tubes were provided for determination. One of the capillary tubes was dipped in human serum, while the other capillary tube was dipped in rabbit serum. The serum samples were each soaked up to a point near the upper end (8–9 cm the way up from the lower end) of its corresponding capillary tube (FIG. 11). The amount of each of the thus-soaked serum samples was about 60 μl. It took 30 minutes for the soaking. When the capillary tubes with the thus-soaked serum samples were exposed to light from an excitation lamp. In the case of the human serum, fluorescence was observed at the zone (k-5) in FIG. 11. However, no fluorescence was observed in the case of the rabbit serum.

Example 12

[1] Materials (1)–(8):
There were used the same materials as those employed in Example 1, [1].

(9) Plunger with a hole:
A hole-defining plunger of the same type as that referred to in Example 2, [1], (9) was employed.

(10) Heparin and EDTA-mixed GB.BSA:
Heparin and EDTA-mixed GB.BSA similar to that referred to in Example 2, [1] was used.

[2] Preparation of capillary tubes for measurements

Five marks were placed on each of the albumin-coated glass capillary tubes, first one at a point 5 mm from the lower end of the albumin-coated glass capillary tubes and then successive four marks upward on the capillary tubes with an interval of 3.5 mm. The polyester fibers (a-1) were packed over the first 5 mm. The lower end of the capillary tube was then connected to a vacuum pump so as to produce a negative pressure within the capillary tube. The heparin and EDTA-mixed GB.BSA (a-1') and, the dianisidine-mixed GB.BSA (a-2) were then sucked and packed successively over the following 3.5 mm spans. In the similar manner, the GB.BSA (a-3), αRb-IgG-HRP mixed GB.BSA (a-4), GB.BSA (a-5) and Rb-IgG-O (a-6) were packed successively. The GB (a-7) were then packed in the remaining space to a point 5 mm the way down form the upper end of the capillary tube, and finally, the polyester fibers were packed over the remaining 5 mm.

[3] Distinction between fresh human blood and fresh rabbit blood:

Two capillary tubes were provided for detection. The lower end of one of the capillary tubes was brought into contact with a nick produced in a part of human ear and that of the other capillary tube was brought into contact with a nick produced in a part of rabbit ear. The human and rabbit bloods were slowly sucked to the zones (a-6) by means of the plungers. The amount of each of the thus-sucked bloods was about 9 µl. It took 20 seconds for the suction. Thereafter, the lower ends of the capillary tubes were dipped in PBS which contained 0.003% of hydrogen peroxide. The hydrogen peroxide containing PBS was soaked up to points near the upper ends (8-9 cm the way up from the lower ends) of the capillary tubes. It took 15 minutes for this soaking. As a result, the zone corresponding to the Rb-IgG-O (a-6) was colored in brown by the human blood. However, no color was observed in the case of the rabbit blood.

EXAMPLE 13

[1] Materials:

(1) Albumin-coated capillary tubes:
The albumin-coated capillary tubes of Example 1, [1], (1) were used.
(2) GB having diameter of 0.1 mm
(3) GB.BSA:
The GB.BSA of Example 1, [1], (3) were used.
(4) Polyester fiber
(5) Dianisidine-mixed GB.BSA:
The dianisidine-mixed GB.BSA of Example 4, [1], (4) were employed. (6) Sodium perborate mixed GB.BSA:
Twelve milligrams of sodium perborate and 10 g of GB.BSA were evenly mixed in a mortar. (7) Glutathione-mixed GB.BSA:
Forty milligrams of glutathione and 10 g of GB.BSA were evenly mixed in a mortar.
(8) Peroxidase conjugated anti-α-fetoprotein antibody (αAFP-HRP):
The αAFP-HRP of Example 7, [1], (6) was used.
(9) αAFP-HRP mixed GB.BSA:
The GB.BSA mixed with αAFP-HRP, of Example 7, [1], (7), were employed.
(10) Anti-α-fetoprotein antibody fixed GB (αAFP-O):
The αAFP-O of Example 7, [1], (8) was used.

[2] Preparation of capillary tubes for measurements

The following capillary tubes were prepared in the same manner as in Example 1, [2].

The polyester fibers (1-1) were packed over the first 5 mm, followed by the packing of the dianisidinemixed GB.BSA (1-2), sodium perborate mixed GB.BSA (1-3), glutathione-mixed GB.BSA (1-4), GB.BSA (1-5), αAFP-HRP mixed GB.BSA (1-6), GB.BSA (1-7) and αAFP-O(1-8) respectively 3.5 mm each. The GB (1-9) were then packed in the remaining space of the capillary tube to a point 5 mm the way down from the upper end of the capillary tube, and the polyester fibers were packed over the remaining 5 mm.

[3] Measurement of α-fetoprotein in serum

Human serum containing α-fetoprotein in an amount of 200 µg per milliliter of the serum was diluted with PBS to a volume ten times its original volume so as to obtain a liquid mixture of human serum and PBS which contains α-fetoprotein at a final concentration of 20 µg per milliliter of the liquid mixture (Sample A) was obtained. In addition, human serum containing α-fetoprotein in an amount of 20 µg per milliliter of the serum (Sample B) and a supernatant obtained by treating 0.5 ml of the serum (which contained α-fetoprotein in an amount of 20 µg per milliliter of the serum) with 50 mg of neutral copper hydroxide (Sample C) were also provided. Namely, three samples were provided. Three capillary tubes were provided. Their lower ends were dipped respectively in Sample A, Sample B and Sample C. These samples were soaked up to points near the upper ends (8-9 cm the way up from the lower ends) of their corresponding capillary tubes. As a result, Sample A gave a brown color to the αAFP-O [(1-8) in FIG. 12], whereas Sample B did not color the αAFP-O [(1-8) in FIG. 12]. On the other hand, a brown color was observed at the αAFP-O [(1-8) in FIG. 12] in the case of Sample C. From the above results, even if a substance which inhibits the above reaction is contained in a sample, the measurement is still feasible provided that the sample is treated beforehand, for example, by its dilution or by an addition of a further substance.

EXAMPLE 14

[1] Materials (1) Albumin-coated glass capillary tubes:
PBS containing bovine serum albumin in an amount of 20 mg per milliliter of the PBS was passed through glass capillary tubes (diameters: 1 mm; lengths: 100 mm). The glass tubes were then aspirated to remove any remaining PBS, followed by air drying.
(2) Glass beads (GB; diameter: 0.17 mm)
A commercial product was used.
(3) GB.BSA:
GB were immersed in PBS containing bovine serum albumin in an amount of 20 mg per milliliter of the PBS. GB were then washed 2-3 times with distilled water, and were thereafter dried.
(4) Polyester fiber:
A commercial product was employed.
(5) $^{125}I$-α-fetoprotein mixed GB.BSA (hereinafter abbreviated as "RI-AFP mixed GB.BSA"):
To the radioactive iodized AFP($^{125}I$) solution (0.9 µCi/bial) which was included in a commercial AFP measurement kit (product of Daiichi Radioisotope Co., Ltd.), 1.0 g of the GB.BSA was added. The resultant mixture was stirred evenly and was then dried over phosphorus pentoxide.
(6) Anti-AFP-GB:
Added to 5 g of the GB was 3 ml of poly-L-lysine (1%). After allowing the resultant mixture to stand at room temperature, it was washed with distilled water. Glutaraldehyde was added to the surface-treated GB and the resultant mixture was left over. Then, it was similarly washed with distilled water. Thereafter, 5 mg of anti-AFP antibody was added to the thus-crosslinked GB. After allowing them to react at room temperature for 2 hours, the reaction product was dried to prepare anti-AFP-GB.
(7) PBS

[2] Preparation of capillary tubes for measurements

From the lower end of each of the albumin-coated glass capillary tubes, five marks were placed with an interval of 3.5 mm. The polyester fibers (m-1) was packed firstly. This lower end was then connected to a vacuum pump to establish a negative pressure within the capillary tube. The GB.BSA (m-2) was then sucked and packed over the next 3.5 mm. Similarly, the RI-AFP mixed GB.BSA (m-3), GB.BSA (m-4) and anti-AFP-GB (m-5) were packed successively 3.5 mm each. The GB.BSA (m-6) were thereafter packed in the remaining space of the capillary tube to a point 5 mm the way down from the upper end of the capillary tube, and then, the polyester fibers (m-7) were packed over the remaining 5 mm. (FIG. 13)

[3] Measurement of α-fetoprotein in serum

Five capillary tubes were provided for measurements. Four of the five capillary tubes were dipped respectively in serum samples having known AFP concentrations of 0, 3.125, 25 and 50 μg/ml respectively. The remaining capillary tube was dipped in a serum sample. The serum samples were respectively soaked up to the zones (m-3) in FIG. 13. The amount of each of the thus-soaked serum samples was 5 μl. Then, the lower ends of the capillary tubes were dipped in PBS so as to soak it to the upper ends of the capillary tubes. It took 10 minutes for the soaking.

After measuring the capillary tubes by means of a gamma counter while holding them with their lower ends down, the sections of the capillary tubes which contained the immobilized substance (m-5) were cut off and were measured by the gamma counter in the same manner.

[4] Results

| Concentration μg/ml | Gamma ray counts (cpm) of capillary tube | |
| --- | --- | --- |
| | Measured before cutting | Measured after cutting |
| AFP 0 | 1226 | 1211 |
| 3.125 | 1219 | 1181 |
| 25 | 1076 | 1071 |
| 50 | 714 | 723 |
| Sample | 768 | 725 |

From the above results, it was observed that the the intensity of the immobilized radioactivity decreased as the AFP concentration increased. It was also able to measure the AFP concentration of the sample as being 55–60 μg/ml.

EXAMPLE 15

[1] Materials (1) Albumin-coated glass capillary tubes:

PBS containing bovine serum albumin in an amount of 20 mg per milliliter of the PBS was passed through glass capillary tubes (diameters: 1 mm; lengths: 100 mm). The glass capillary tubes were aspirated to remove any remaining liquid, followed by air drying.

(2) Glass beads (GB; diameter: 0.17 mm):
A commercial product was used.

(3) GB.BSA:
GB were immersed in PBS containing bovine serum albumin in an amount of 20 mg per milliliter of the PBS. The GB were then washed 2–3 times with distilled water and were thereafter dried.

(4) Polyester fiber:
A commercial product was employed.

(5) $^{125}$I-anti-α-fetoprotein antibody mixed GB.BSA (hereinafter abbreviated as "RI-anti-AFP mixed GB.BSA"):

To the radioactive iodized α-fetoprotein antibody ($^{125}$I) (lyophilized product; 0.9 μCi/bial) which was included in a commercial AFP measurement kit (product of Daiichi Radioisotope Co., Ltd.), 1.0 g of the GB.BSA was added. The resultant mixture was stirred evenly.

(6) Anti-AFP-GB:

Three milliliters of poly-L-lysine (1%) were added to 5 g of GB. After allowing the resultant mixture to stand at room temperature, it was washed with distilled water. Glutaraldehyde was then added to the resultant surface-treated GB. The thus-prepared mixture was allowed to stand. Then, it was washed with distilled water. Thereafter, 5 mg of anti-AFP antibody was added to the thus-crosslinked GB. After allowing them to react to each other at room temperature for 2 hours, the reaction product was dried to prepare anti-AFP-GB.

(7) PBS

[2] Preparation of capillary tubes for measurements

Five marks were placed on each of the albumin-coated glass capillary tubes, with an interval of 3.5 mm from the lower end of the capillary tubes. The polyester fiber (n-1) was packed firstly. The lower end was connected to a vacuum pump to produce a negative pressure within the capillary tube. The GB.GSA (n-2) were then sucked and packed over the next 3.5 mm. In the same manner, the RI-anti-AFP mixed GB.BSA (n-3), GB.BSA (n-4) and anti-AFP-GB (n-5) were successively packed 3.5 mm each. The GB.BSA (n-6) were then packed in the remaining space in the capillary tube to a point 5 mm the way down from the upper end of the capillary tube. Finally, the polyester fibers (n-7) were also packed over the remaining 5 mm. (FIG. 14)

[3] Measurement of α-fetoprotein in serum

Seven capillary tubes were provided for measurements. The lower ends of six of the seven capillary tubes were dipped respectively in AFP samples having known concentrations of 0, 3, 10, 100, 500 and 5000 ng/ml. The remaining one capillary tube was dipped in a serum sample. The serum samples were each soaked up to the zone (n-4). The amount of each of the thus-soaked serum samples was about 5 μl. Then, the lower ends of the capillary tubes were soaked in PBS so as to soak the PBS to points near the upper ends of the capillary tubes. It took 10 minutes.

After measuring the capillary tubes by means of a gamma counter while holding them with their lower ends down, the sections of the capillary tubes which contained the immobilized substance (n-5) were cut off and were measured by the gamma counter in the same manner.

(4) Results:

| Concentration ng/ml | Gamma ray counts (cpm) of capillary tube | |
| --- | --- | --- |
| | Measured before cutting | Measured after cutting |
| AFP 0 | 564 | 110 |
| 3 | 585 | 112 |
| 10 | 628 | 138 |
| 100 | 776 | 154 |
| 500 | 841 | 191 |

-continued

| Concentration ng/ml | Gamma ray counts (cpm) of capillary tube | |
|---|---|---|
| | Measured before cutting | Measured after cutting |
| 5000 | 856 | 585 |
| Sample | 727 | 149 |

From the above results, it was observed that the intensity of the immobilized radioactivity increased as the AFP concentration increased. It was also able to measure the AFP concentration of the sample as being 50–100 ng/ml.

EXAMPLE 16

[1] Materials (1) Albumin-coated glass capillary tubes:

0.01-M Phosphate-buffered saline (pH 7.2) containing boxine serum albumin in an amount of 20 mg per milliliter of the saline was passed through glass capillary tubes (diameters: 1 mm; lengths: 100 mm). The glass capillary tubes were then aspirated to remove any remaining liquid, followed by air drying.

(2) Glass beads (diameter: 0.17 mm; hereinafter abbreviated as "GB"):

A commercial product was employed.

(3) Albumin-coated GB (hereinafter abbreviated as "GB.BSA"):

GB were immersed in PBS which contained bovine serum albumin in an amount of 20 mg per milliliter of the PBS. GB were washed 2–3 times with distilled water and were then dried.

(4) Polyester fiber:

A commercial product was used.

(5) $^{125}$I-α-fetoprotein reagent (hereinafter abbreviated as "RI-AFP"):

The radioactive iodized α-fetoprotein ($^{125}$I) 0.9 μCi/bial) which was included in a commercial α-fetoprotein (hereinafter abbreviated as "AFP") measurement kit (product of Daiichi Radioisotope Co., Ltd.) was used as was.

(6) Anti-AFP antibody fixed GB (hereinafter abbreviated as "anti-AFP-GB"):

Three milliliters of poly-L-lysine (1%) were added to 5 g of GB. After allowing the resultant mixture to stand at room temperature, it was washed with distilled water. Glutaraldehyde was then added to the surface-treated GB. After allowing the the resulting mixture, it was similarly washed with distilled water. Thereafter, 5 mg of anti-AFP antibody was added to the thus-crosslinked GB. After allowing them to react at room temperature for 2 hours, the reaction product was dried to prepare anti-AFP-GB.

(7) PBS

[2] Preparation of capillary tubes for measurement:

From the lower end of each of the albumin-coated glass capillary tubes, five marks were placed with an interval of 3.5 mm. The polyester fibers (o-1) were firstly packed. The lower end of the capillary tube was connected to a vacuum pump to produce a negative pressure within the capillary tube. Then, the GB.BSA (o-2) were sucked and packed over the next 10.5 mm. In the same manner, the anti-AFP-GB (o-3) were packed over the next 3.5 mm. Then, the GB.BSA (o-4) were packed in the remaining space of the capillary tube to a point 5 mm the way down from the upper end thereof, and finally, the polyester fibers (o-5) were also packed over the remaining 5 mm. Then, another mark was placed at a point 3.5 mm the way up from the lower end. (FIG. 15)

[3] Measurement of α-fetoprotein in serum

Seven capillary tubes were provided for measurements. The lower ends of six of the seven capillary tubes were dipped respectively in serum samples having known AFP concentrations of 0, 30, 300 ng/ml and 1, 25 and 50 μg/ml. The remaining one capillary tube was dipped in a serum sample. These serum samples were soaked up respectively to the zones (o-3) in FIG. 15. The amount of each of the thus-soaked serum samples was 5 μl. Then, the lower ends of the capillary tubes were dipped in the RI-AFP so as to soak up the RI-AFP. The amount of each of the thus-soaked RI-AFP was also 5 μl. Thereafter, the lower ends of the capillary tubes were dipped in PBS so that the PBS was soaked up to the upper ends of the capillary tubes. It took 15 minutes for the soaking.

After measuring the capillary tubes by means of a gamma counter while holding them with their lower ends down, the sections of the capillary tubes which contained the immobilized substance (o-5) were cut off and were measured by the gamma counter in the same manner.

(4) Results

| Concentration per ml | Gamma ray counts (cpm) of capillary tube | |
|---|---|---|
| | Measured before cutting | Measured after cutting |
| AFP 0 ng | 947 | 864 |
| 30 | 943 | 830 |
| 300 | 890 | 755 |
| 1 μg | 740 | 664 |
| 25 | 301 | 173 |
| 50 | 247 | 109 |
| Sample | 608 | 510 |

From the above results, it was observed that the the intensity of the immobilized radioactivity decreased as the AFP concentration increased. It was also able to measure the AFP concentration of the sample as being 2.5–3 μg/ml.

EXAMPLE 17

[1] Materials: (1) Albumin-coated glass capillary tubes:

PBS containing bovine serum albumin in an amount of 20 mg per milliliter of the PBS was passed through glass capillary tubes (diameters: 1 mm; lengths: 100 mm). The glass capillary tubes were then aspirated to remove any remaining liquid, followed by air drying.

(2) GB (diameter: 0.17 mm):

A commercial product was employed.

(3) GB.BSA:

GB were immersed in PBS which contained bovine serum albumin in an amount of 20 mg per milliliter of the PBS. GB were washed 2–3 times with distilled water and were then dried.

(4) Polyester fiber:

A commercial product was used.

(5) $^{125}$I-α-fetoprotein antibody reagent (hereinafter abbreviated as "RI-anti-AFP"):

The radioactive iodized α-fetoprotein antibody ($^{125}$I) (lyophilized product; 0.9 μCi/bial) which was included in a commercial α-fetoprotein measurement kit (product of Daiichi Radioisotope Co., Ltd.) was provided, to which 500 μl of distilled water was added to dissolve the former uniformly.

(6) Anti-AFP-GB:

Three milliliters of poly-L-lysine (1%) were added to 5 g of GB. After allowing the resultant mixture to stand at room temperature, it was washed with distilled water. Glutaraldehyde was then added to the surface-treated GB. After allowing the the resulting mixture, it was similarly washed with distilled water. Thereafter, 5 mg of anti-AFP antibody was added to the thus-cross-linked GB. After allowing them to react at room temperature for 2 hours, the reaction product was dried to prepare anti-AFP-GB.

(7) PBS

[2] Preparation of capillary tubes for measurement:

From the lower end of each of the albumin-coated glass capillary tubes, five marks were placed with an interval of 3.5 mm. The polyester fibers (p-1) were firstly packed. The lower end of the capillary tube was connected to a vacuum pump to produce a negative pressure within the capillary tube. Then, the GB.BSA (p-2) were sucked and packed over the next 10.5 mm. In the same manner, the anti-AFP-GB (p-3) were packed over the next 3.5 mm. Then, the GB.BSA (p-4) were packed in the remaining space of the capillary tube to a point 5 mm the way down from the upper end of the capillary tube, and finally, the polyester fibers (p-5) were also packed over the remaining 5 mm. (FIG. 16)

[3] Measurement of α-fetoprotein in serum

Seven capillary tubes were provided for measurements. The lower ends of six of the seven capillary tubes were dipped respectively in liquid mixtures of 5 μl portions of serum samples having known AFP concentrations of 0, 3, 10, 30, 100, and 300 ng/ml and 5 μl portions of the RI-AFP. The remaining one capillary tube was dipped in a liquid mixture which had been obtained by mixing 5 μl of a serum sample and 5 μl of the RI-AFP. These mixtures were soaked up to the capillary tubes. It took 30 seconds for the soaking. Then, the lower ends of the capillary tubes were dipped in PBS so as to soak up the PBS to the upper ends of the capillary tubes. It took 10 minutes for the soaking.

After measuring the capillary tubes by means of a gamma counter while holding them with their lower ends down, the sections of the capillary tubes which contained the immobilized substance (p-3) were cut off and were measured by the gamma counter in the same manner.

(4) Results:

| Concentration ng/ml | Gamma ray counts (cpm) of capillary tube | |
|---|---|---|
| | Measured before cutting | Measured after cutting |
| AFP 0 | 773 | 62 |
| 3 | 850 | 63 |
| 10 | 1179 | 109 |
| 30 | 1235 | 241 |
| 100 | 1255 | 397 |
| 300 | 2136 | 870 |
| Sample | 1335 | 330 |

From the above results, it was observed that the the intensity of the immobilized radioactivity increased as the AFP concentration increased. It was also able to measure the AFP concentration of the sample as being about 50 ng/ml.

We claim:

1. An immunoassay for detecting the presence of a target substance in a sample by immunoreaction, which comprises:

(1) providing a capillary tube, wherein said capillary tube contains therein at least (a) a first solid matrix containing a labelled first antibody or antigen capable of binding to said target substance, and (b) a second solid matrix having immobilized thereon a second antibody or antigen capable of binding said target substance, (2) contacting the end of said capillary tube closest to said first solid matrix with a liquid sample suspected of containing said targe substance to be measured, and allowing said sample material to migrate in said capillary tube by capillary action, thereby subjecting any target substance present in said liquid sample to immunoreaction with said first antibody or antigen in said first solid matrix to form an immunocomplex, followed by further migration of said immunocomplex and unreacted labelled first antibody or antigen into said second solid matrix, wherein any labelled immunocomplex is bound to said immobilized second antibody or antigen, and (c) detecting the immobilized labelled immunocomplex bound to said second matrix material.

2. An immunoassay for detecting the presence of a target substance in a sample by immunoreaction, which comprises:

(1) providing a capillary tube, wherein said capillary tube contains therein at least (a) a first solid matrix containing a labelled antibody or antigen capable of binding to said target substance, and (b) a second solid matrix having immobilized thereon said target substance, (2) contacting the end of said capillary tube closest to said first solid matrix with a liquid sample suspected of containing a target substance to be measured, and allowing said sample material to migrate in said capillary tube by capillary action, thereby subjecting any target substance present in said liquid sample to immunoreaction with said labelled antibody or antigen in said first solid matrix to form an immunocomplex, followed by further migration of said immunocomplex and unreacted labelled antibody or antigen into said second solid matrix, wherein any free labelled antibody or antigen is bound to said immobilized target substance, and (3) detecting the immobilized labelled antibody or antigen bound to said second matrix material.

3. An immunoassay for detecting the presence of a target substance in a sample by immunoreaction, which comprises:

(1) providing a capillary tube, wherein said capillary tube contains therein at least (a) a first solid matrix containing labelled target substance, and (b) a second solid matrix having immobilized thereon an antibody or antigen capable of binding said target substance or said labelled target substance, (2) contacting the end of said capillary tube closest to said first solid matrix with a liquid sample suspected of containing a target substance to be measured, and allowing said sample material to migrate in said capillary tube by capillary action, allowing a competitive reaction to occur in said second solid matrix, whereby the amount of bound labelled target substance is inversely proportional to the amount of said target substance in said sample, and
(3) detecting the immobilized labelled target substance bound to said second matrix material.

4. An immunoassay according to claim 1, 2, or 3, wherein said antibodies are monoclonal antibodies.

5. An immunoassay according to claims 1, 2 or 3 wherein said first and second solid matrices are constituted by spherical beads or polygonal beads.

* * * * *